United States Patent
Furuki et al.

(10) Patent No.: US 7,880,879 B2
(45) Date of Patent: Feb. 1, 2011

(54) OPTICAL MEASURING DEVICE

(75) Inventors: Motohiro Furuki, Tokyo (JP); Shingo Imanishi, Kanagawa (JP); Masataka Shinoda, Tokyo (JP)

(73) Assignee: Sony Corporation, Tokyo (JP)

( * ) Notice: Subject to any disclaimer, the term of this patent is extended or adjusted under 35 U.S.C. 154(b) by 72 days.

(21) Appl. No.: 12/349,931

(22) Filed: Jan. 7, 2009

(65) Prior Publication Data

US 2010/0020321 A1    Jan. 28, 2010

(30) Foreign Application Priority Data

Jan. 8, 2008    (JP) .......................... P2008-001338

(51) Int. Cl.
*G01N 21/00* (2006.01)
(52) U.S. Cl. ..................................... 356/337
(58) Field of Classification Search ................. 356/337
See application file for complete search history.

(56) References Cited

U.S. PATENT DOCUMENTS

2006/0073076 A1 *  4/2006  Ichiki et al. ................... 422/73

FOREIGN PATENT DOCUMENTS

| JP | 2003-004752 | 1/2003 |
| JP | 2003-302330 | 10/2003 |
| JP | 2004-085323 | 3/2004 |
| JP | 2004-257756 | 9/2004 |

* cited by examiner

*Primary Examiner*—Roy Punnoose
(74) *Attorney, Agent, or Firm*—K&L Gates LLP (57) ABSTRACT

An optical measuring device is provided. The optical measuring device irradiates a sample flowing in a channel with light, and detecting light emitted from the sample, wherein the light is applied while scanned at least from one side wall to another side wall of the channel in a direction of width of the channel, and scattered light at a preset threshold value or higher is detected as scattered light from edge parts in the direction of width of the channel.

5 Claims, 12 Drawing Sheets

OPTICAL MEASURING DEVICE

CROSS REFERENCES TO RELATED APPLICATIONS

The present application claims priority to Japanese Patent Application JP 2008-001338, filed in the Japan Patent Office on Jan. 8, 2008, the entire contents of which being incorporated herein by reference.

BACKGROUND

The present application relates to an optical measuring device for optically detecting samples such as minute particles or the like, and particularly to techniques of irradiating samples flowing within a channel and detecting light emitted from the samples.

An optical measuring device such as a flow cytometer or the like is generally used to identify living body related minute particles such as cells, microorganisms, liposomes and the like (see "Cellular Engineering Extra Number Experiment Protocol Series Flow Cytometry at Will," Second Edition, Shujunsha Co. Ltd., issued on Aug. 31, 2006, edited by Hiromitsu Nakauchi for example). The flow cytometer is a device that identifies a plurality of minute particles one by one by irradiating the minute particles flowing in a line within a channel with laser light of a specific wavelength and detecting fluorescence or scattered light emitted from each minute particle.

Specifically, in a flow cell, a laminar flow is formed by a sample liquid including minute particles to be measured and a sheath liquid flowing on the periphery of the sample liquid, and a slight pressure difference is produced between the sample liquid and the sheath liquid, whereby the plurality of minute particles included in the sample liquid are arranged in a line. When the flow cell is irradiated with laser light in this state, the minute particles pass the laser light so as to traverse the laser beam one by one. At this time, fluorescence and/or scattered light excited by the laser light and emitted from each minute particle is detected by using an electrooptic detector.

In addition, there is a method of using a substrate having a fine channel formed therein in place of a flow cell (see Japanese Patent Laid-Open Nos. 2003-302330 and 2004-85323 hereinafter be referred to as Patent Documents 1 and 2, for example). Existing microchips described in Patent Documents 1 and 2 have one or a plurality of channels through which to make samples to be measured flow in a transparent substrate. For example, two sheath liquid introducing channels join a sample liquid introducing channel from both sides to form one sample channel, and a laminar flow is formed at the junction part of these channels.

Figure 13:
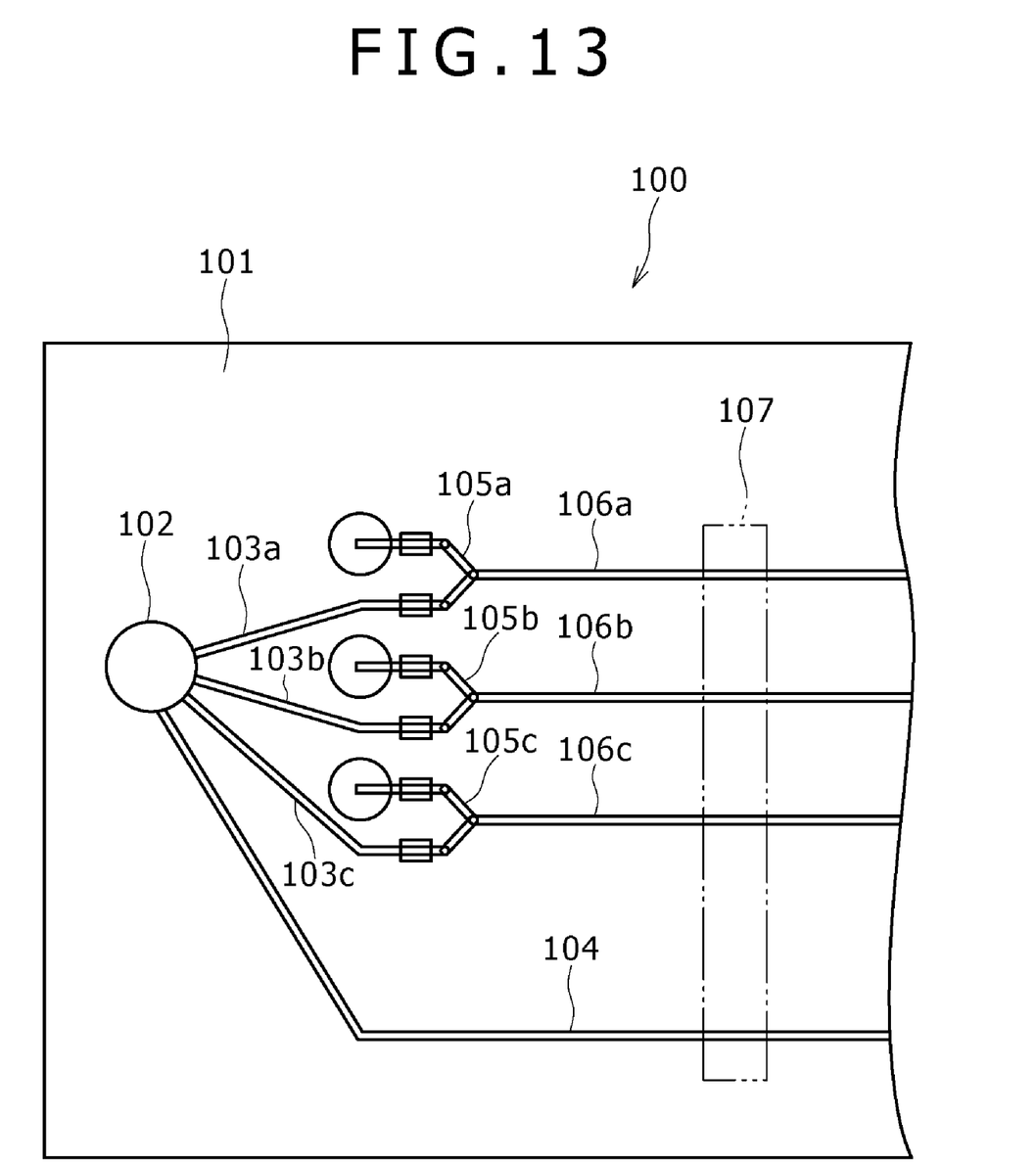
FIG. 13 is a plan view of a channel constitution of an existing microchip described in Patent Document 3.

Another existing microchip has been proposed which has a reference channel through which to make a liquid including no samples flow in addition to a channel through which to make a sample liquid including samples to be measured flow in order to improve detection accuracy (see Japanese Patent Laid-Open No. 2003-4752 hereinafter be referred to as Patent Document 3). FIG. 13 is a plan view of a channel constitution of the existing microchip described in Patent Document 3. As shown in FIG. 13, the microchip 100 described in Patent Document 3 has a specimen introducing opening 102 for introducing a specimen such as blood or the like on a substrate 101, and has specimen channels 103a to 103c and a reference channel 104 connected to the specimen introducing opening 102. Of these channels, the specimen channels 103a to 103c are joined by reagent channels 105a to 105c through which to make a reagent to react with the specimen flow to form merged channels 106a to 106c. In addition, a detecting section 107 is provided for each of the merged channels 106a to 106c and the reference channel 104.

When measurement is made using the above-described microchip 100, a specimen such as blood or the like is supplied from the specimen introducing opening 102, so that the specimen is made to flow through the specimen channels 103a to 103c and the reference channel 104. In addition, a reagent to react with the specimen is made to flow through the reagent channels 105a to 105c, so that the specimen and the reagent react with each other in the merged channels 106a to 106c. Then, the detecting section 107 irradiates the respective liquids flowing through the merged channels 106a to 106c and the reference channel 104 with light, and detects scattered light or reflected light emitted as a result of the irradiation.

In the microchip 100 described in Patent Document 3, the reference channel 104 is not joined by a reagent channel, and thus the unreacted specimen flows through the reference channel 104. Thus, a signal detected from the reference channel 104 corresponds to a noise component of signals detected from the merged channels 106a to 106c. Only a signal originating from the reaction with the reagent can be obtained by performing signal processing that subtracts the detection signal from the reference channel 104 from the detection signals from the merged channels 106a to 106c.

SUMMARY

However, the existing techniques described above have the following problems. In the existing optical measuring devices such as the flow cytometer and the like, a particular position of the channel formed in the flow cell or the substrate is irradiated with laser light in the form of a spot, and samples flow within the laser spot. However, the flowing speed of the samples and the irradiation intensity of the laser light differ depending on the flowing positions of the samples, so that variations occur in the intensity of detected light. The above-described problem tends to occur especially when the samples to be measured are minute particles such as cells, beads or the like, the width of the channel or the laminar flow is larger than the particle diameter of the minute particles, and the minute particles are not aligned.

In addition, also in the case of using a microchip having a plurality of fine channels formed in a same substrate, particular positions of the respective channels are irradiated with laser light in the form of a spot. However, it is difficult to make the pitches of the fine channels constant in a manufacturing process, and manufacturing errors tend to occur in each lot. Thus, the laser light is not applied to a preset position, and the irradiation position of the laser light is varied in each channel, so that detection accuracy is lowered.

It is accordingly desirable to provide an optical measuring device that can easily detect edge parts in a direction of width of a channel through which to make samples flow, and detect the samples with high accuracy.

According to an embodiment of the present application, there is provided an optical measuring device for irradiating a sample flowing in a channel with light, and detecting light emitted from the sample, wherein the light is applied while scanned at least from one side wall to another side wall of the channel in a direction of width of the channel, and scattered light at a preset threshold value or higher is detected as scattered light from edge parts in the direction of width of the channel.

The optical measuring device according to the above-described embodiment of the present application scans the light from one side wall to the other side wall of the channel in the direction of width of the channel. Therefore the positions of the edge parts in the direction of width of the channel can be easily identified from the intensity of detected scattered light.

The optical measuring device can identify a flowing position of the sample in the channel from the scattered light from the edge parts in the direction of width of the channel and scattered light from the sample.

When a plurality of channels for a sample to be measured to flow in are arranged, it is desirable to further provide a reference channel in which the sample does not flow at an outermost part in a direction of arrangement of the channels, also irradiate the reference channel with light while scanning the light at least from one side wall to another side wall of the reference channel in a direction of width of the reference channel, and detect scattered light at a preset threshold value or higher as scattered light from edge parts in the direction of width of the reference channel.

In this case, the reference channel and the other channels may be different from each other in shape or intensity of detected scattered light.

According to an embodiment, the positions of edge parts in a direction of width of a channel can be easily identified, and a detection signal can be corrected by identifying the flowing position of a sample in the channel on the basis of information on the positions of the edge parts. It is therefore possible to improve the strength of the detection signal, detection sensitivity, detection accuracy, and the like.

Additional features and advantages are described herein, and will be apparent from the following Detailed Description and the figures.

DETAILED DESCRIPTION

The present application will be described in further detail below with reference to the accompanying drawings.

The present inventor has found, as a result of diligently making experiments and studies to solve the above-described problems, that correction of a detection signal, adjustment of a laser light irradiating position, and the like are made possible by detecting end parts (hereinafter referred to as edge parts) in a direction of width of a channel and determining the flowing position of samples within the channel, the width and pitch of each channel, and the like on the basis of a result of the detection.

Accordingly, the present inventor considered methods for detecting edge parts of a channel, and has confirmed that an edge part can be detected by providing a reflective film such as a metallic film or the like on an inner surface of a channel and detecting light reflected from the reflective film or by fixing a phosphor on an inner surface of a channel and detecting fluorescence emitted from the phosphor. However, these methods each require addition of a new process during manufacturing of a substrate, and thus may invite a decrease in yield of the substrate and an increase in manufacturing cost.

In addition, when a plurality of channels are formed in a same substrate, similar signals are obtained from all of the channels. It is therefore difficult to determine whether the start position of laser light is correct and know which of detection signals originate from edge parts of channels at both ends. This problem can be solved by providing a reference channel on the outside of a channel where a sample liquid containing samples flows (which channel will hereinafter be referred to as a sample channel), and filling the reference channel with for example beads modified by a fluorescent dye, so that different signals are obtained from the sample channel and the reference channel. However, even in this case, a problem remains in that the fluorescent dye is degraded and thus the strength of the detection signal from the reference channel is not stable.

Accordingly, the present inventor further considered methods for detecting edge parts in a direction of width of a channel without a reflective film or a fluorescent dye being provided on an inner surface of the channel. This has led to the present application. Specifically, an optical measuring device according to an embodiment applies light while scanning at least from one side wall to another side wall in a direction of width of a channel, and detects at least scattered light of light emitted as a result of the application of the light. Then, scattered light at a preset threshold value or higher is distinguished as scattered light from an edge part of a channel.

Description will first be made of an optical measuring device according to a first embodiment of the present invention. The measuring device according to the present embodiment passes a sample liquid through a sample channel provided in a flow cell or a substrate, and optically measures a kind, a state, size and the like of samples included in the sample liquid. The measuring device according to the present embodiment includes: a light irradiating section for irradiating the sample channel with light; and a light detecting section for detecting at least scattered light.

The light irradiating section in the optical measuring device according to the present embodiment applies light while scanning at least from one side wall to another side wall in a direction of width of the sample channel. The light applied from the light irradiating section is not particularly limited, and can be selected from light of various wavelengths such as laser light, ultraviolet light, infrared light, visible light and the like according to the kind of samples or the like.

For example, when the applied light is laser light, the light irradiating section may include a laser oscillator, a mirror, a condensing lens and the like, and be configured such that laser light emitted from the laser oscillator and reflected by the mirror in a direction of the channel is condensed by the condensing lens and applied. Applicable as the laser oscillator used at this time are for example a solid-state laser such as a YAG (Yttrium Aluminum Garnet) laser or the like, a semiconductor laser, and a femtosecond laser.

The light detecting section has a light detecting device of a CCD (Charge Coupled Device) and a PMT (Photo-Multiplier Tube), for example. The light detecting section detects at least scattered light of light emitted from the edge parts of the sample channel and samples. The optical measuring device according to the present embodiment can further detect fluorescence in addition to the scattered light in the light detecting section. In addition, the optical measuring device according to the present embodiment may be provided with another light detecting section for detecting fluorescence separately from the light detecting section for the scattered light.

Figure 1A:
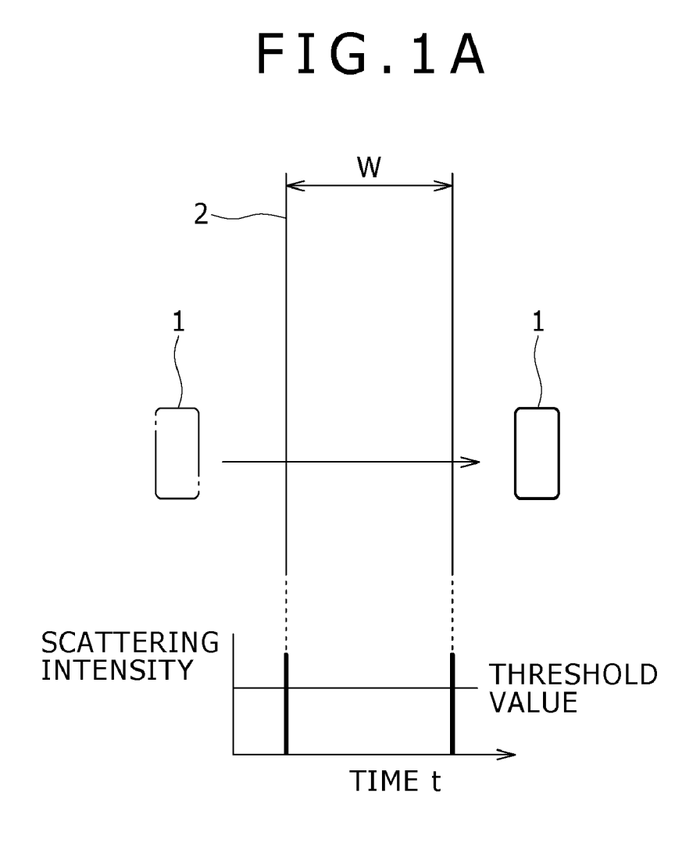
FIGS. 1A and 1B are diagrams showing scattering intensity detected when laser light is scanned in a direction of width of a channel, FIG. 1A showing scattering intensity in a case where no minute particles are present in a scanning area, and FIG. 1B showing scattering intensity in a case where minute particles are present in the scanning area.
Figure 1B:
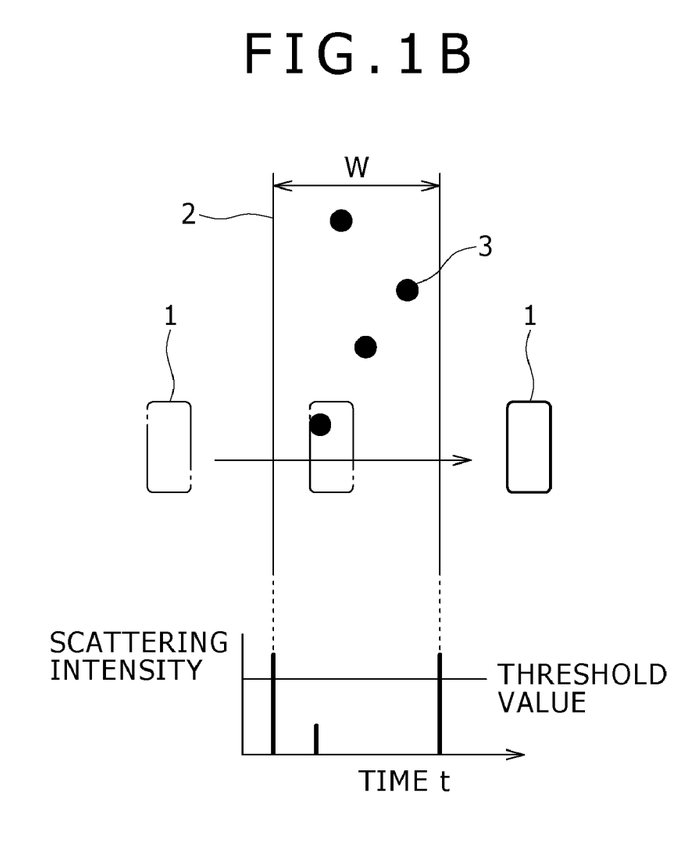

The operation of the optical measuring device according to the present embodiment, that is, a measuring method using the optical measuring device according to the present embodiment will next be described by taking as an example a case of applying laser light and detecting minute particles such as cells, microbeads and the like. FIGS. 1A and 1B are diagrams showing the intensity of scattered light detected when laser light is scanned in a direction of width of a channel. FIG. 1A shows scattering intensity in a case where no minute particles are present in a scanning area. FIG. 1B shows scattering intensity in a case where minute particles are present in the scanning area.

As shown in FIGS. 1A and 1B, the optical measuring device according to the present embodiment continuously irradiates a sample channel 2 with laser light 1 while scanning the laser light 1 at least from one side wall to another side wall in a direction of width w of the sample channel 2. The scattered light detecting section then detects scattered light from the edge parts of the sample channel 2 and a minute particle 3. At this time, as shown in FIG. 1B, the intensity of scattered light emitted from the edge parts of the sample channel 2 is higher than the intensity of scattered light emitted from the minute particle 3.

Accordingly, the optical measuring device according to the present embodiment sets a threshold value in a range higher than a maximum value of scattered light from samples in advance, identifies scattered light exhibiting an intensity equal to or higher than the threshold value as scattered light from the edge parts of the sample channel 2, and distinguishes the scattered light from the edge parts of the sample channel 2 from scattered light from minute particles 3. Incidentally, it suffices for the threshold value set in this case to be a value by which the scattered light from the samples and the scattered light from the edge parts can be distinguished from each other, and the threshold value can be set as appropriate according to the kind of the samples, the shape of the channel, a substrate material, and the like.

By thus scanning the irradiation light in the direction of width of the channel and detecting scattered light emitted as a result of the scanning of the irradiation light, the positions of the edge parts of the sample channel 2 can be identified easily. Thus, with the positions of the edge parts as a reference, the width w of the channel, the flowing positions of the minute particles 3 within the channel, and the like can be identified, and further a detection signal can be corrected on the basis of information on the flowing positions of the minute particles 3 and a flow rate distribution and/or the intensity distribution of the laser light or the like. It is therefore possible to improve the strength of the detection signal, detection sensitivity, detection accuracy, and the like.

For example, when a strip-shaped laminar flow is formed, and detection is performed by laser light irradiation, the amount of light of a laser spot after passing through an acoustooptic element (Acousto-Optic Modulator; AOM) is large at a central part of the channel, and is decreased as the laser spot comes closer to an edge. Therefore a detection signal originating from a sample flowing in the vicinity of a side surface of the channel may be smaller than a detection signal originating from a sample flowing in the central part of the channel. In such a case, it suffices to correct the signal quantity of detected light such as fluorescence, scattered light and the like and sensitivity on the basis of the flowing position of each sample within the channel and the distribution of intensity of the laser after passing through the AOM.

In addition, because the flow rate of the strip-shaped laminar flow is highest at a central part of the flow, and becomes lower with decrease in distance to an edge, a detection signal originating from a sample flowing in the vicinity of a side surface of the channel may be larger than a detection signal originating from a sample flowing in the central part of the channel. In such a case, it suffices to correct the scanning speed of the laser light according to the flowing speed of samples within the channel.

Incidentally, while FIGS. 1A and 1B represent a case where the laser light is scanned once, the present invention is not limited to this, but the laser light may be scanned a plurality of times in the direction of width of the channel. Thereby the SN ratio of a detection signal can be improved. In addition, while the present embodiment has described a case where samples are minute particles such as cells, beads and the like, the present invention is not limited to this, but is applicable to detection of DNA, protein, blood, pieces of tissue, and the like.

Further, it is also possible first to allow a liquid to flow in a state of not including minute particles 3, detect the edge parts of the sample channel 2, and thereby identify the positions of the edge parts of the sample channel 2, as shown in FIG. 1A, and then to allow a liquid including the minute particles 3 to flow, and identify the position of each minute particle 3 by comparing the positions of the edge parts, as shown in FIG. 1B.

Figure 2:
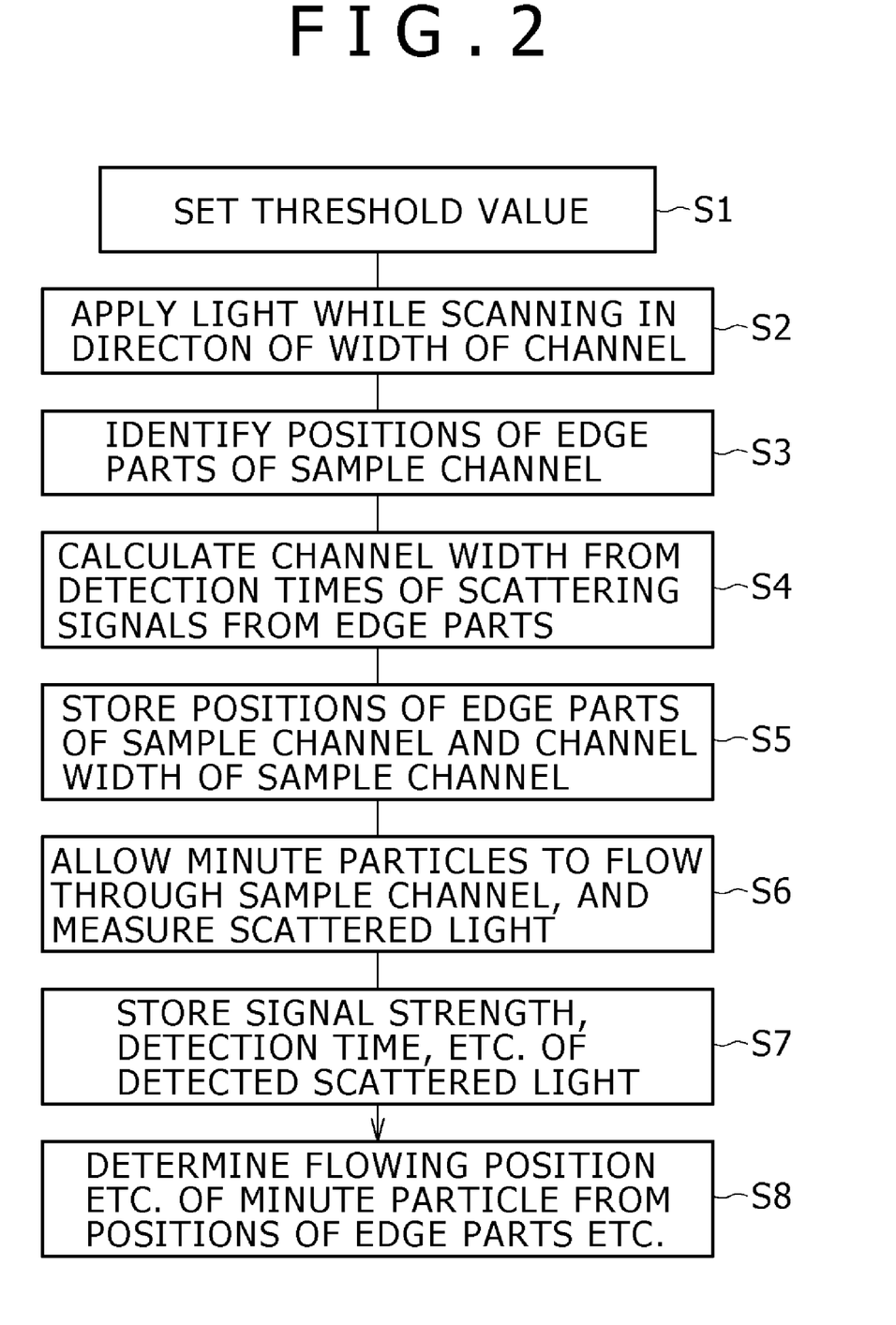
FIG. 2 is a flowchart of an example of a procedure when minute particles are measured after the edge parts of each channel are detected.

FIG. 2 is a flowchart of an example of the procedure. When minute particles 3 are measured after the edge parts of the sample channel 2 are identified, a threshold value for scattering signal strength is set first as shown in FIG. 2, for example, in order to distinguish scattered light from the edge parts from scattered light from other parts (step S1). Next, the laser light 1 is continuously applied while scanned at least from one side wall to the other side wall in the direction of width w of the sample channel 2 (step S2). Incidentally, a time for setting the threshold value in step S1 is not limited to a time before the laser light application in step S2. The threshold value may be set during the laser light application or after the laser light application. Therefore, it is also possible to perform the above-described step S2 first, and then perform step S1.

Thereafter, for example, scattering signals of two highest intensities of scattered light exhibiting intensities equal to or higher than the threshold value are recognized as those of light from the edge parts of the sample channel 2, and the positions of the edge parts are identified (step S3). Next, the channel width of the sample channel 2 is calculated from a time (hereinafter referred to as a detection time) from a time of a start of the scanning of the laser light to the detection of the scattered light recognized as scattered light from the edge parts (step S4). The value is stored in a recording medium or the like (step S5).

Next, the laser light is applied while a liquid including minute particles 3 is made to flow through the sample channel 2, and scattered light from the minute particles 3 is detected (step S6). The signal strength, detection time and the like of the detected scattered light are stored on the recording medium or the like (step S7). Then, the flowing position of each minute particle 3 is determined on the basis of the positions of the edge parts of the sample channel 2 which positions are obtained in step S3, and the flowing speed of the minute particle 3 is determined from the channel width obtained in step S4 (step S8).

Description will next be made of an optical measuring device according to a second embodiment. The optical measuring device according to the foregoing first embodiment is not limited to cases of one sample channel, but is also applicable to cases of making measurement using a substrate having a plurality of channels formed therein. When such a substrate is used, it is desirable to provide reference channels at outermost parts in a direction of arrangement of sample channels, and detect the positions of edge parts of each sample channel from the positions of edge parts of each reference channel.

Figure 3:
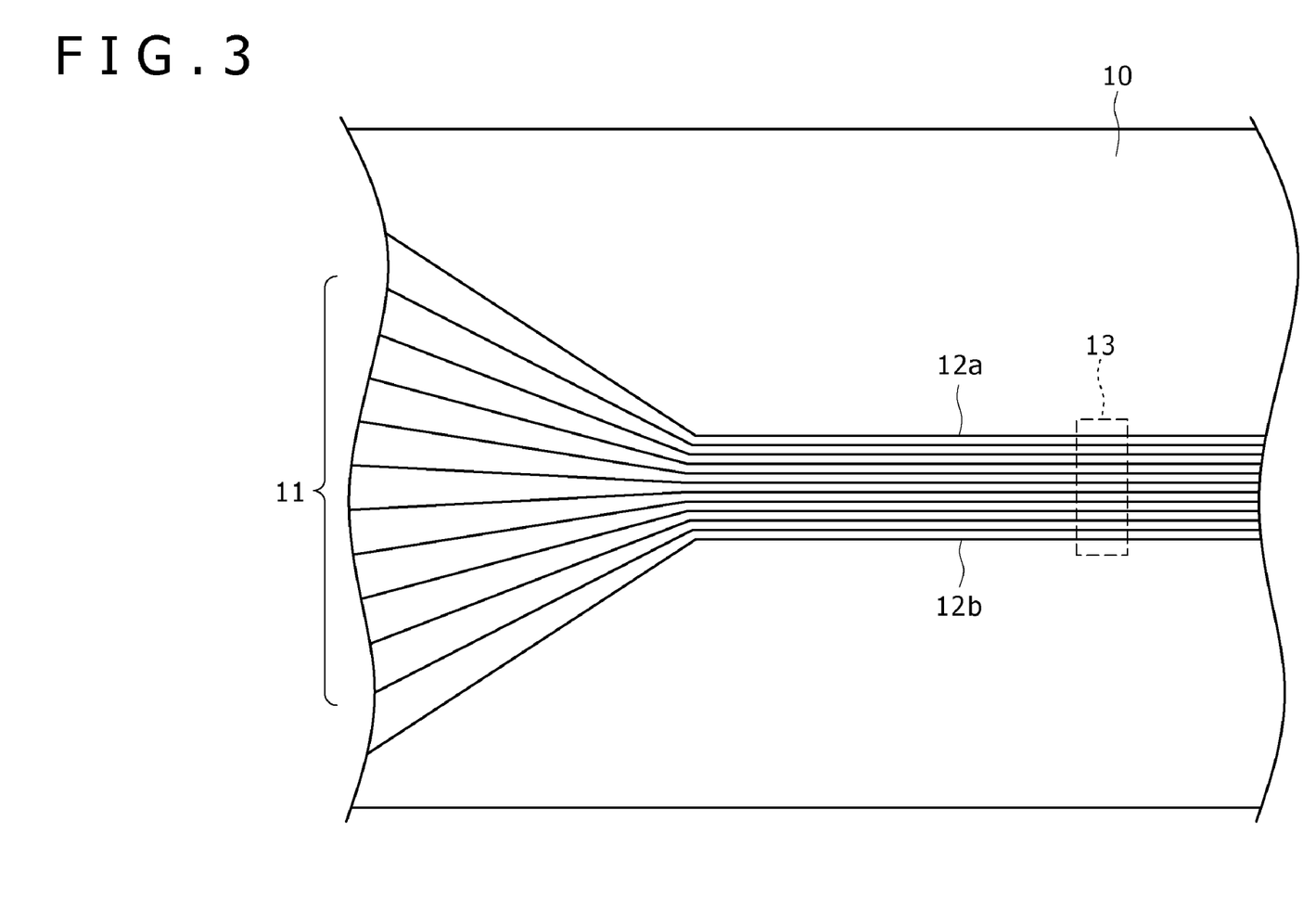
FIG. 3 is a plan view of an example of a channel constitution of a substrate used by an optical measuring device according to a second embodiment.
Figure 4:
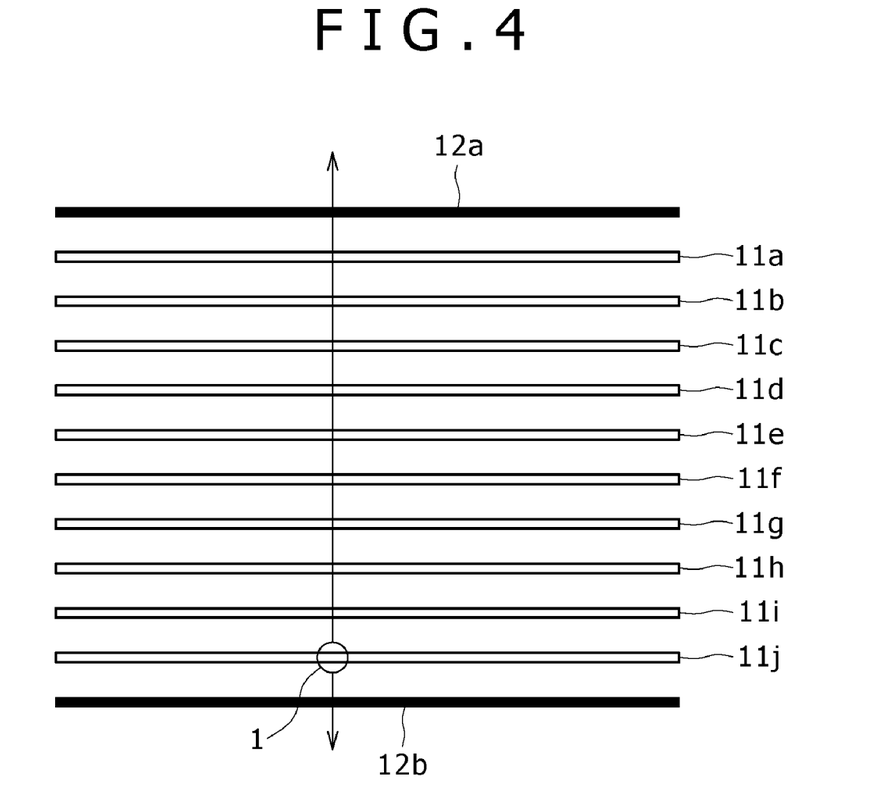
FIG. 4 is an enlarged plan view of a detecting section shown in FIG. 3.

FIG. 3 is a plan view of an example of a constitution of channels in a substrate used by the optical measuring device according to the present embodiment. FIG. 4 is an enlarged plan view of a detecting section of the substrate. The optical measuring device according to the present embodiment makes measurement using the substrate 10 in which reference channels 12a and 12b are provided on the outside of sample channels 11 shown in FIG. 3. In the detecting section 13 of the substrate 10, as shown in FIG. 4, the plurality of sample channels 11a to 11j are formed at fixed intervals, and the reference channel 12a and the reference channel 12b are formed on the outside of the sample channel 11a and the sample channel 11j, respectively, at outermost parts in a direction of arrangement of the sample channels 11a to 11j. A liquid not including samples, a liquid emitting scattered light or fluorescence different from that of a sample liquid, or the like is made to flow through these reference channels 12a and 12b as required.

A light irradiating section irradiates all of the sample channels 11a to 11j and the reference channels 12a and 12b with light such as laser light or the like while scanning the light at least from one side wall to another side wall in a direction of width of each channel. The light detecting section detects at least scattered light emitted from the edge parts of each channel and samples.

Figure 5:
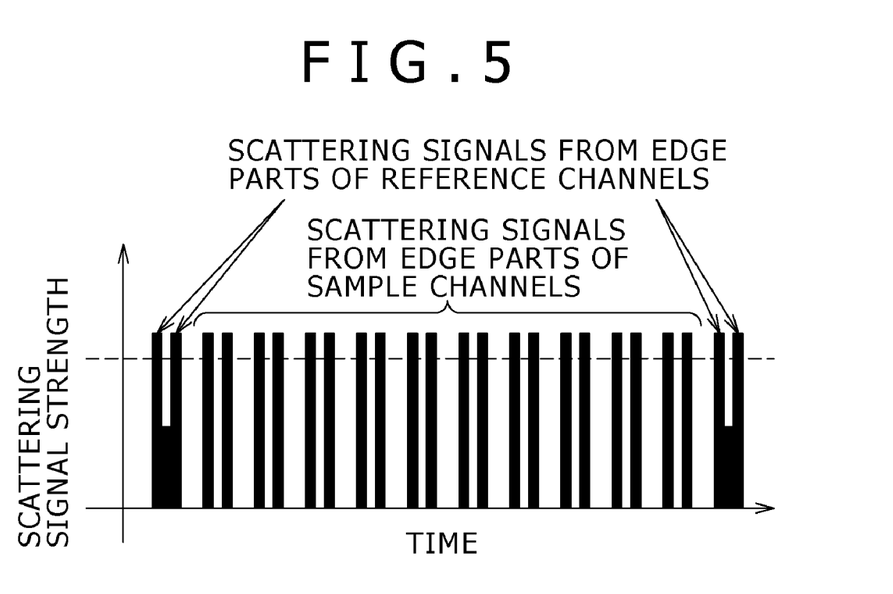
FIG. 5 is a diagram showing intensity of scattered light detected by the optical measuring device according to the second embodiment.

FIG. 5 is a diagram showing intensity of scattered light detected by the optical measuring device according to the present embodiment. By thus scanning the irradiation light in the direction of width of the channels, scattering signals from the edge parts of each channel can be obtained as shown in FIG. 5, and thus the positions of the edge parts of each channel can be identified. At this time, for example, a liquid from which scattered light more intense than that of the sample liquid is obtained is made to flow through the reference channels 12a and 12b so that detection signals obtained from the sample channels 11a to 11j are different from detection signals obtained from the reference channels 12a and 12b. It is thereby possible to easily determine whether the detected scattered light of edge parts originates from the sample channels 11a to 11j or from the reference channels 12a and 12b.

Figure 6:
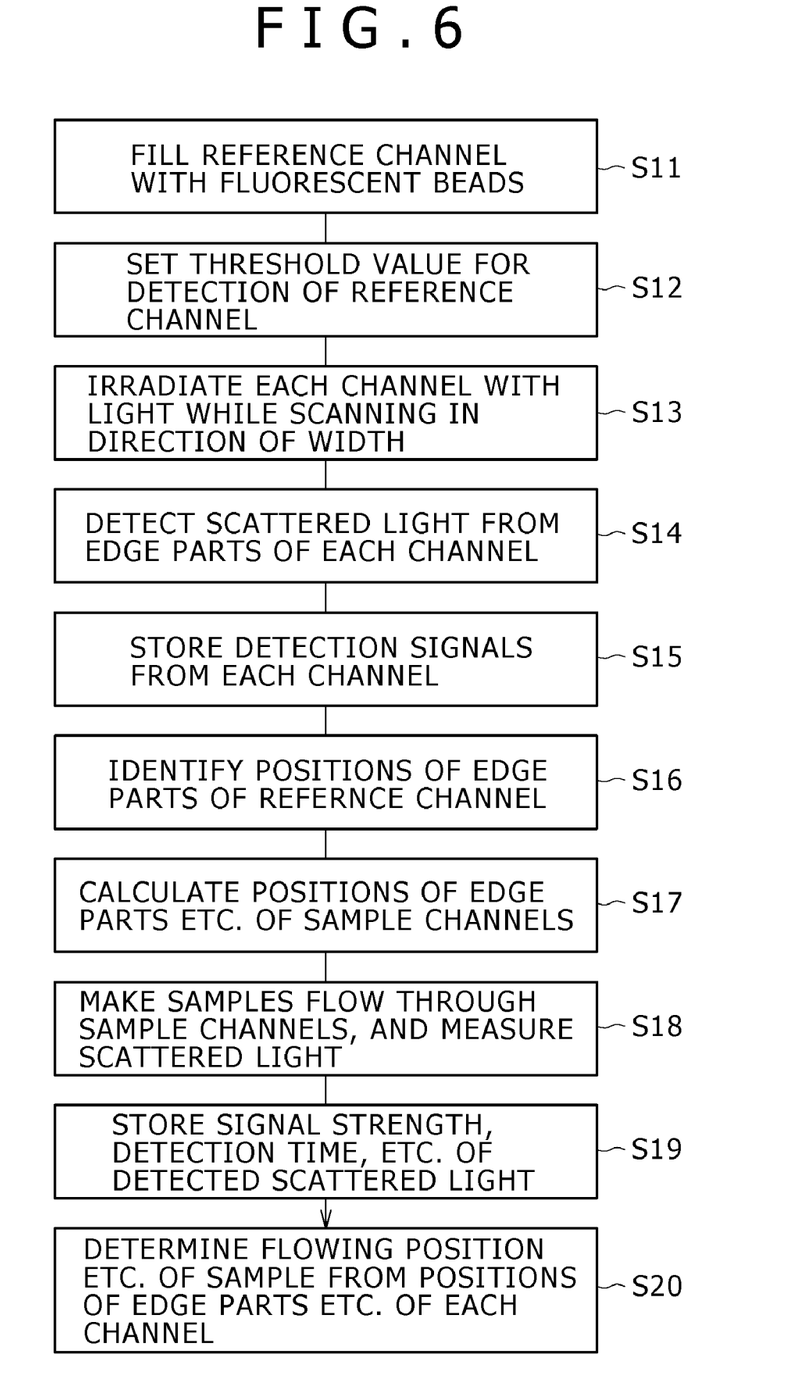
FIG. 6 is a flowchart of an example of a procedure when samples are measured after the edge parts of each channel are detected in a case where the measurement is made using the substrate shown in FIG. 3.

Incidentally, also in the case of using the substrate in which a plurality of channels as shown in FIG. 3 are formed, as in the foregoing first embodiment, while the edge parts of each channel can be detected simultaneously with the measurement of samples, the sample measurement can also be performed after the positions of the edge parts of each channel are identified. FIG. 6 is a flowchart of an example of a procedure in this case. When the positions of the edge parts of each channel are identified in advance, as shown in FIG. 6, the reference channels 12a and 12b are first filled with beads to which a fluorescent dye is fixed (hereinafter abbreviated to fluorescent beads) so that scattered light from the reference channels 12a and 12b is different from scattered light from the sample channels 11 (step S11).

Next, a threshold value is set so as to detect only the scattered light of the fluorescent beads within the reference channels (step S12). Thereafter, each channel is irradiated with light while scanned at least from one side wall to another side wall in the direction of width of each channel (step S13), and scattered light emitted from the fluorescent beads and scattered light emitted from the edge parts of each channel are detected (step S14). These values are stored on a recording medium or the like (step S15). Incidentally, a time for setting the threshold value in step S12 is not limited to a time before the light irradiation in step S13. The threshold value may be set during the laser light irradiation or after the laser light irradiation. Therefore, it is also possible to reverse the order of step S12 and step S13 described above.

Then, for example, scattering signals of two highest intensities of scattered light exhibiting intensities equal to or higher than the threshold value are recognized as those of light from the edge parts of the reference channels 12a and 12b, and the positions of the edge parts of the reference channels 12a and 12b are identified (step S16). Further, the positions of the edge parts, the channel width, and the central position in the direction of width of each of the sample channels 11a to 11j are calculated on the basis of the detection times of the reference channels 12a and 12b (step S17). As a result of the above process, the positions of the edge parts of each channel have been identified. Therefore scattered light from the edge parts of the channels can be easily distinguished from scattered light originating from samples within the channels in a subsequent process.

Next, light is applied while a liquid including samples is made to flow through each of the sample channels 11a to 11j, and scattered light from the samples is detected (step S18). The signal strength, detection time and the like of the detected scattered light are stored on the recording medium or the like (step S19). Then, in which of the sample channels a sample originates flowed, and the flowing position of the sample within the channel are calculated on the basis of information on the positions of the edge parts of each of the sample channels 11a to 11j which positions are obtained in step S17, and further the flowing speed of the samples in each channel is calculated from the channel width and the like of each of the sample channels 11a to 11j (step S20).

As described above in detail, the optical measuring device according to the present embodiment identifies the positions of the edge parts of each sample channel on the basis of information on the positions of the edge parts of the reference channels. Therefore, even when there are manufacturing variations in channel intervals, the positions of samples flowing through each sample channel can be detected accurately. Thus, measurement can be performed with higher accuracy.

In addition, the optical measuring device according to the present embodiment can calculate the width w and pitch of each channel accurately by scanning the irradiation light using a controlled polygon, a galvanometer mirror or the like.

Further, when a liquid flowing through a channel is a laminar flow, relative speed from the center can also be grasped. This facilitates adjustment of a focusing amount of samples by a sheath liquid and adjustment of a balance of the sheath liquid.

Figure 7A:
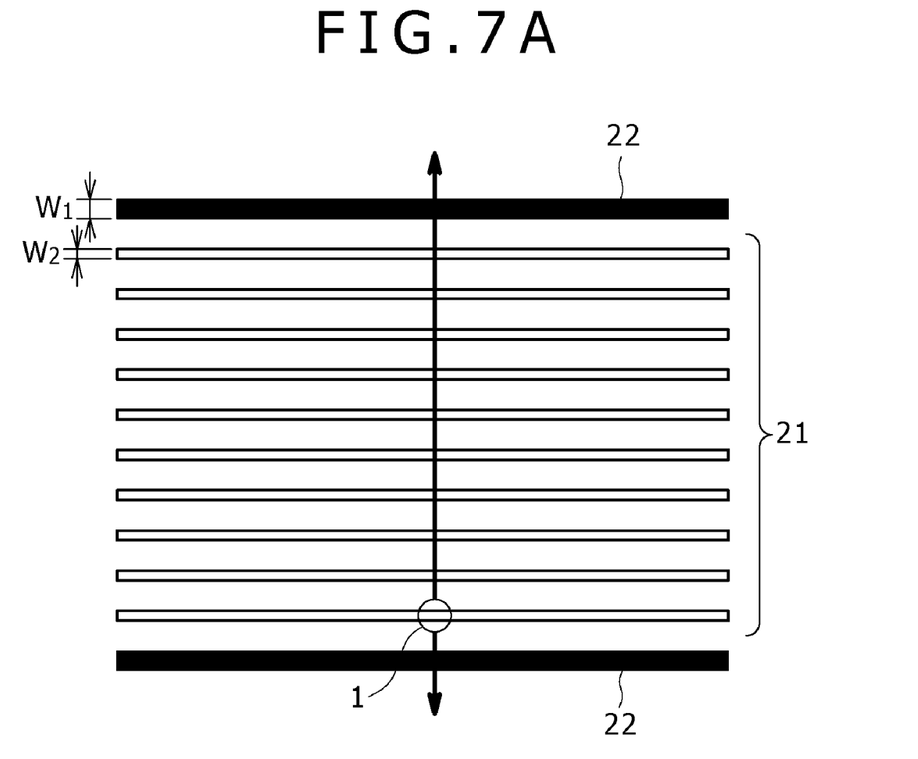
FIG. 7A is a diagram showing a substrate in which sample channels are different from reference channels in channel width.
Figure 7B:
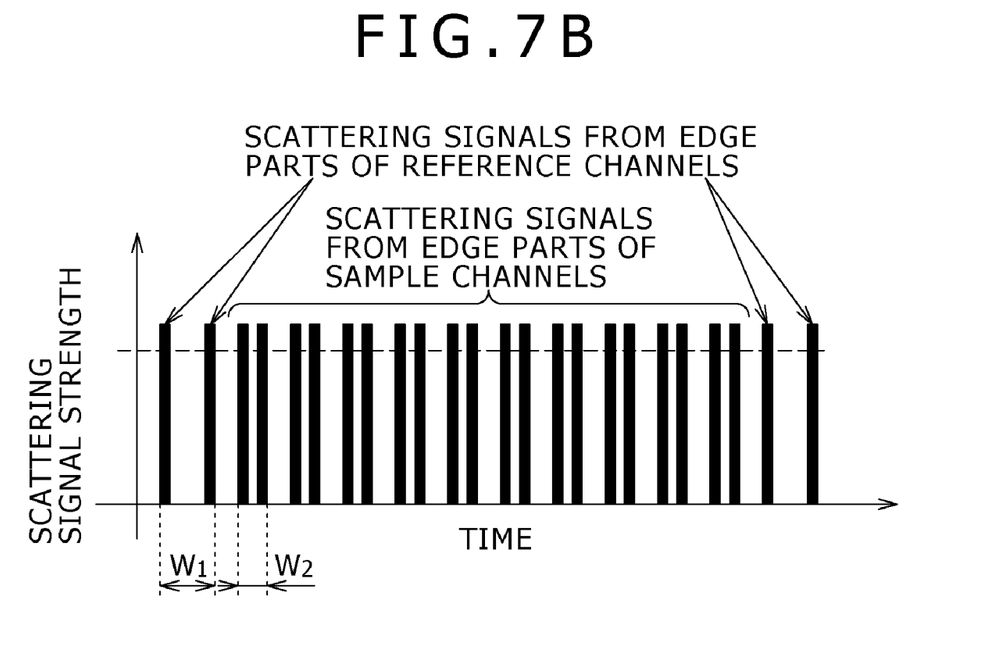
FIG. 7B is a diagram showing scattering intensity detected when the substrate of FIG. 7A is used.

It is to be noted that the substrate used by the optical measuring device according to the present embodiment is not limited to the constitution shown in FIG. 3 and FIG. 4. FIG. 7A is a diagram showing a substrate in which sample channels are different from reference channels in channel width. FIG. 7B is a diagram showing scattering intensity detected when the substrate of FIG. 7A is used. For example, when the width of reference channels 22 is made wider than the width of sample channels 21 as shown in FIG. 7A, an interval $W_1$ of scattering signals from edge parts of the reference channels 22 is wider than an interval $W_2$ of scattering signals from edge parts of the sample channels 21, as shown in FIG. 7B.

Thus, the substrate shown in FIG. 7A makes it possible to easily distinguish the reference channels 22 and the sample channels 21 from each other by using a difference between the signal intervals without filling the reference channels 22 with microparticles, fluorescent beads, a fluorescent liquid or the like, or without making a liquid exhibiting scattering different from that of a sample liquid flow through the reference channels 22. In addition, such wide reference channels are formed at lower cost than existing because machining, molding or the like can be used. As a result, high-precision measurement can be performed at low cost.

Figure 8A:
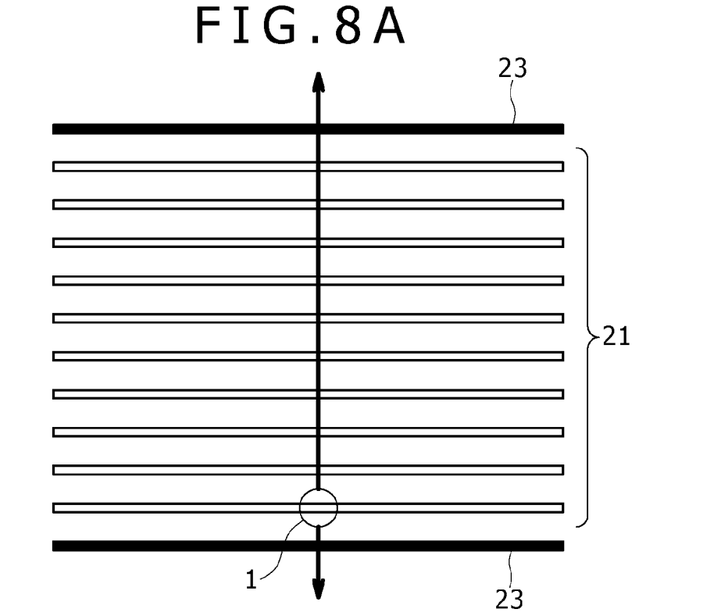
FIG. 8A is a diagram showing a substrate in which sample channels are different from reference channels in channel depth.
Figure 8B:
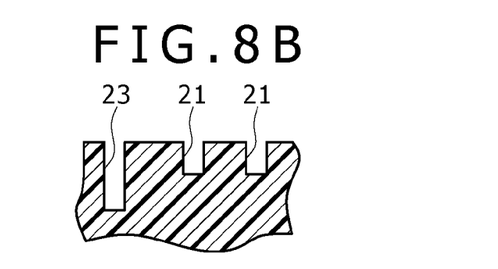
FIG. 8B is a sectional view of the shape of the channels.
Figure 8C:
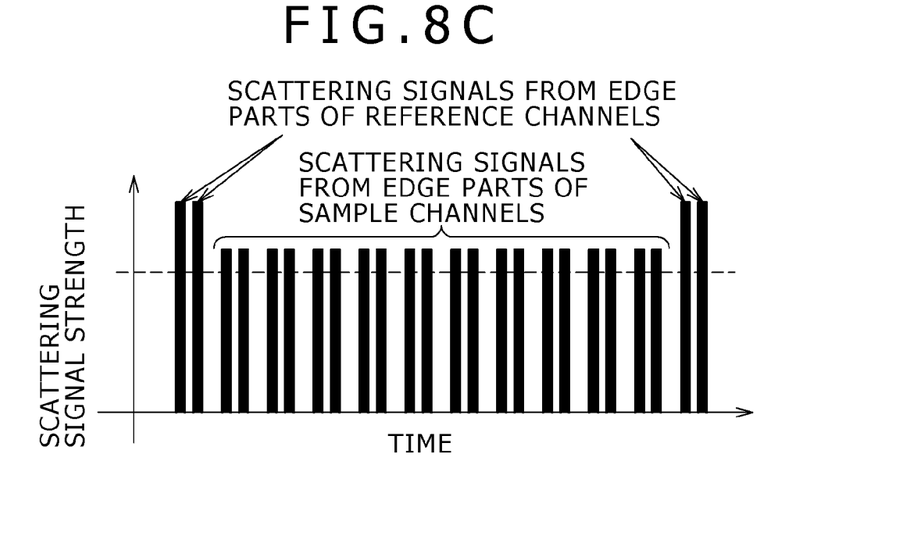
FIG. 8C is a diagram showing scattering intensity detected when the substrate of FIG. 8A is used.

FIG. 8A is a diagram showing a substrate in which sample channels are different from reference channels in channel depth. FIG. 8B is a sectional view of the shape of the channels. FIG. 8C is a diagram showing scattering intensity detected when the substrate of FIG. 8A is used. In addition, as shown in FIGS. 8A and 8B, not only the channel width but also the depth of reference channels 23 may be greater than that of sample channels 21. Thereby, as shown in FIG. 8C, the strength of scattering signals from the edge parts of the reference channels 23 becomes greater than the strength of scattering signals from the edge parts of the sample channels 21. It is thus possible to easily distinguish the reference channels 23 from the sample channels 21.

Figure 9A:
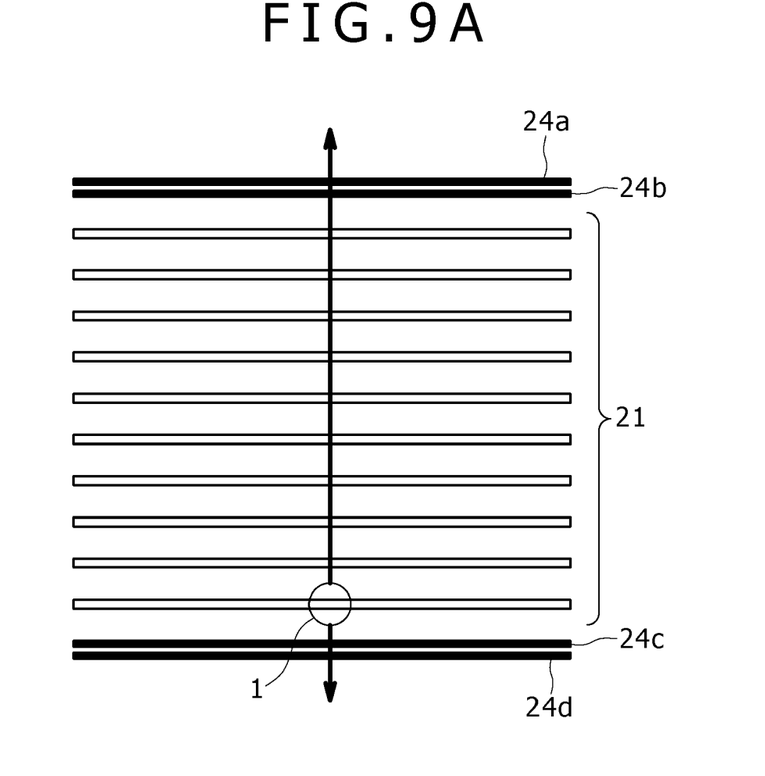
FIG. 9A is a diagram showing a substrate in which a plurality of reference channels are provided on one side.
Figure 9B:
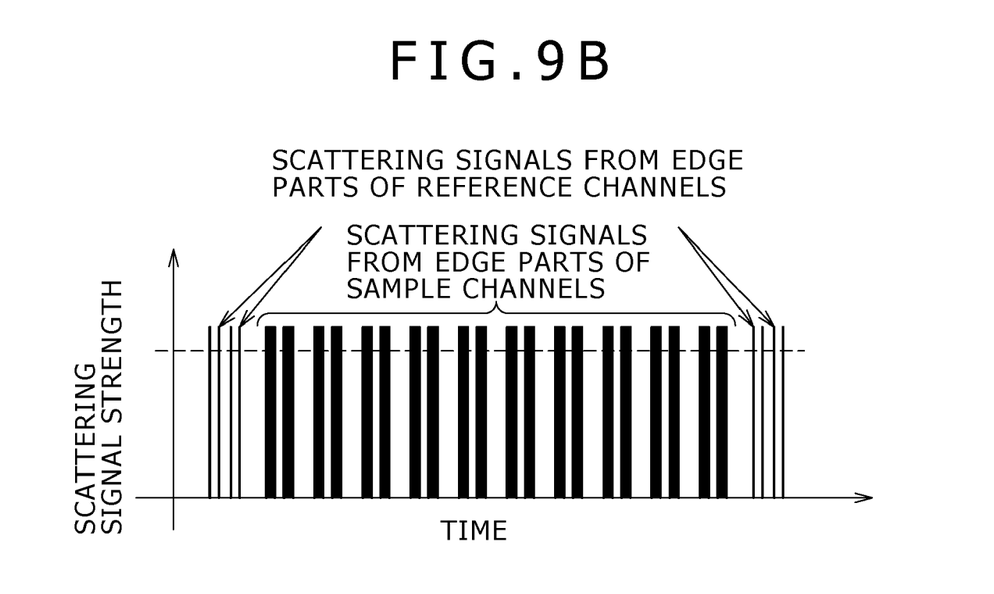
FIG. 9B is a diagram showing scattering intensity detected when the substrate of FIG. 9A is used.

FIG. 9A is a diagram showing a substrate in which a plurality of reference channels are provided on one side. FIG. 9B is a diagram showing scattering intensity detected when the substrate of FIG. 9A is used. Further, as shown in FIG. 9A, two or more minute reference channels 24a to 24d can be provided on the outside of sample channels 21. In this case, as shown in FIG. 9B, scattering signals from the edge parts of the reference channels 24a to 24d and scattering signals from the edge parts of the sample channels 21 can be distinguished from each other by intervals of the signals.

Figure 10A:
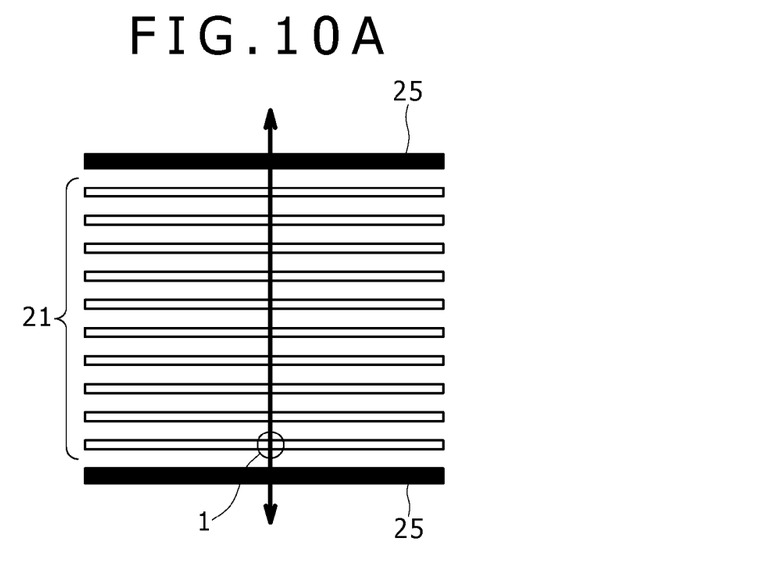
FIG. 10A is a plan view of a substrate in which sample channels are different from reference channels in sectional shape.
Figure 10B:
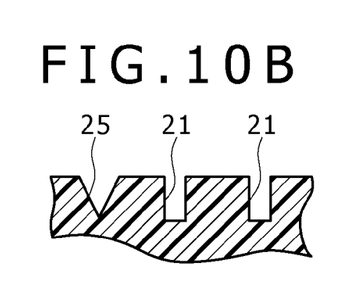
FIG. 10B and FIG. 10C are sectional views of an example of the shape of the channels.
Figure 10C:
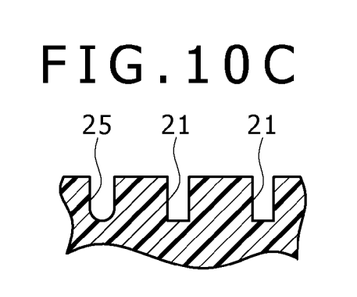
Figure 10D:
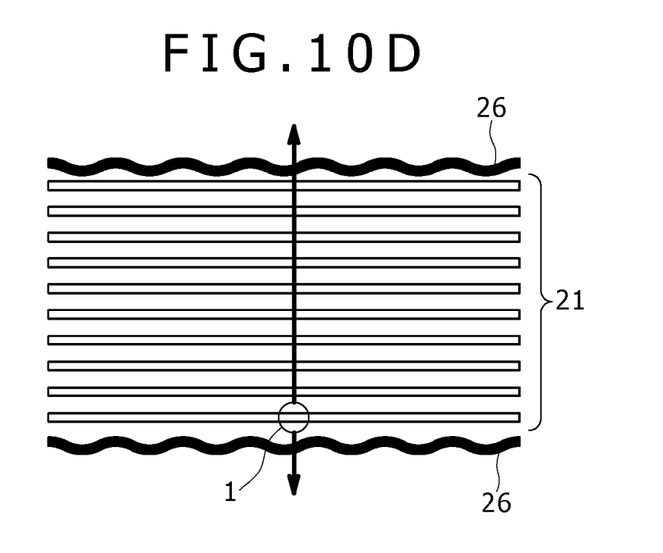
FIG. 10D is a diagram showing a substrate in which reference channels in the form of a curve are formed as viewed in a plan view.
Figure 11A:
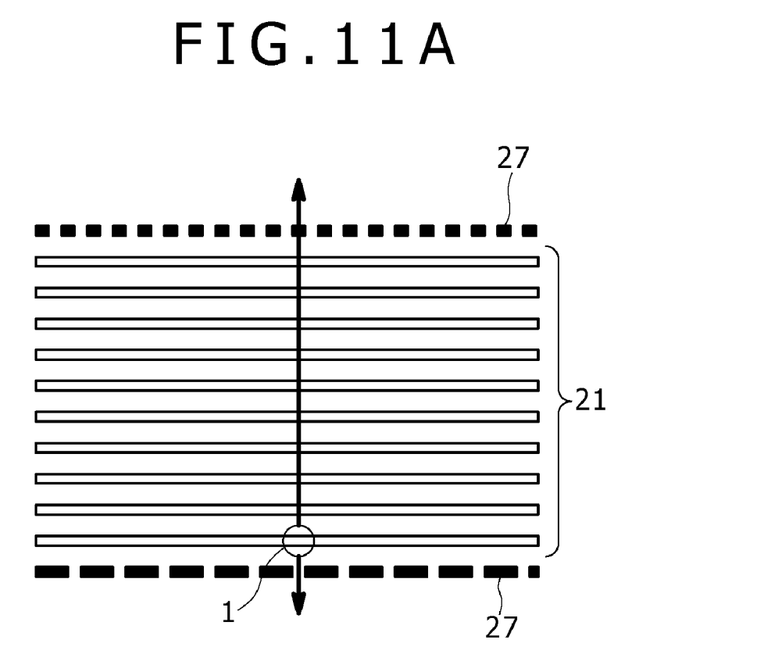
FIG. 11A is a diagram showing a substrate in which reference channels in the form of a broken line are formed as viewed in a plan view.
Figure 11B:
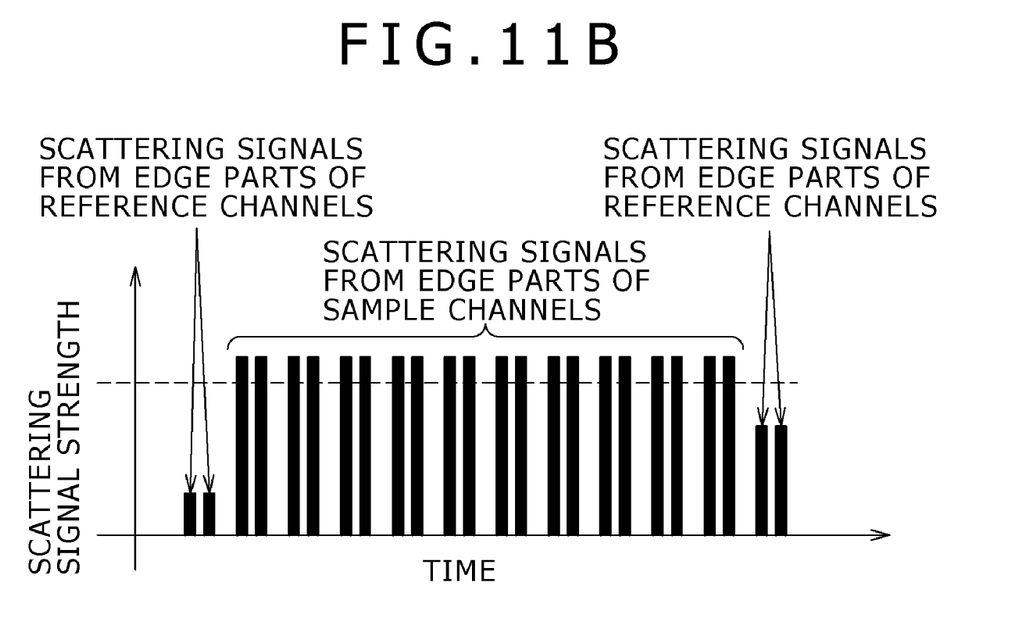
FIG. 11B is a diagram showing scattering intensity detected when the substrate of FIG. 11A is used.

FIG. 10A is a plan view of a substrate in which sample channels are different from reference channels in sectional shape. FIG. 10B and FIG. 10C are a sectional view of an example of the shape of the channels. FIG. 10D and FIG. 11A are diagrams showing a substrate in which reference channels in the form of a curve or in the form of a broken line are formed as viewed in a plan view. FIG. 11B is a diagram showing scattering intensity detected when the substrate of FIG. 11A is used. Further, as in the substrates shown in FIGS. 10A to 10C, sample channels 21 and reference channels 25 are made different from each other in sectional shape perpendicular to a flowing direction. Alternatively, as in the substrates shown in FIG. 10D and FIG. 11A, sample channels 21 and reference channels 26 and 27 can be made different from each other in sectional shape parallel with a substrate surface.

In this case, as shown in FIG. 11B, for example, scattering signals from the edge parts of the reference channels 27 can be distinguished from scattering signals from the edge parts of the sample channels 21 by signal strength of the scattering signals. The position of irradiation light with respect to the reference channels 27 can be determined by asymmetry of the scattering signals from the reference channels 27.

Figure 12:
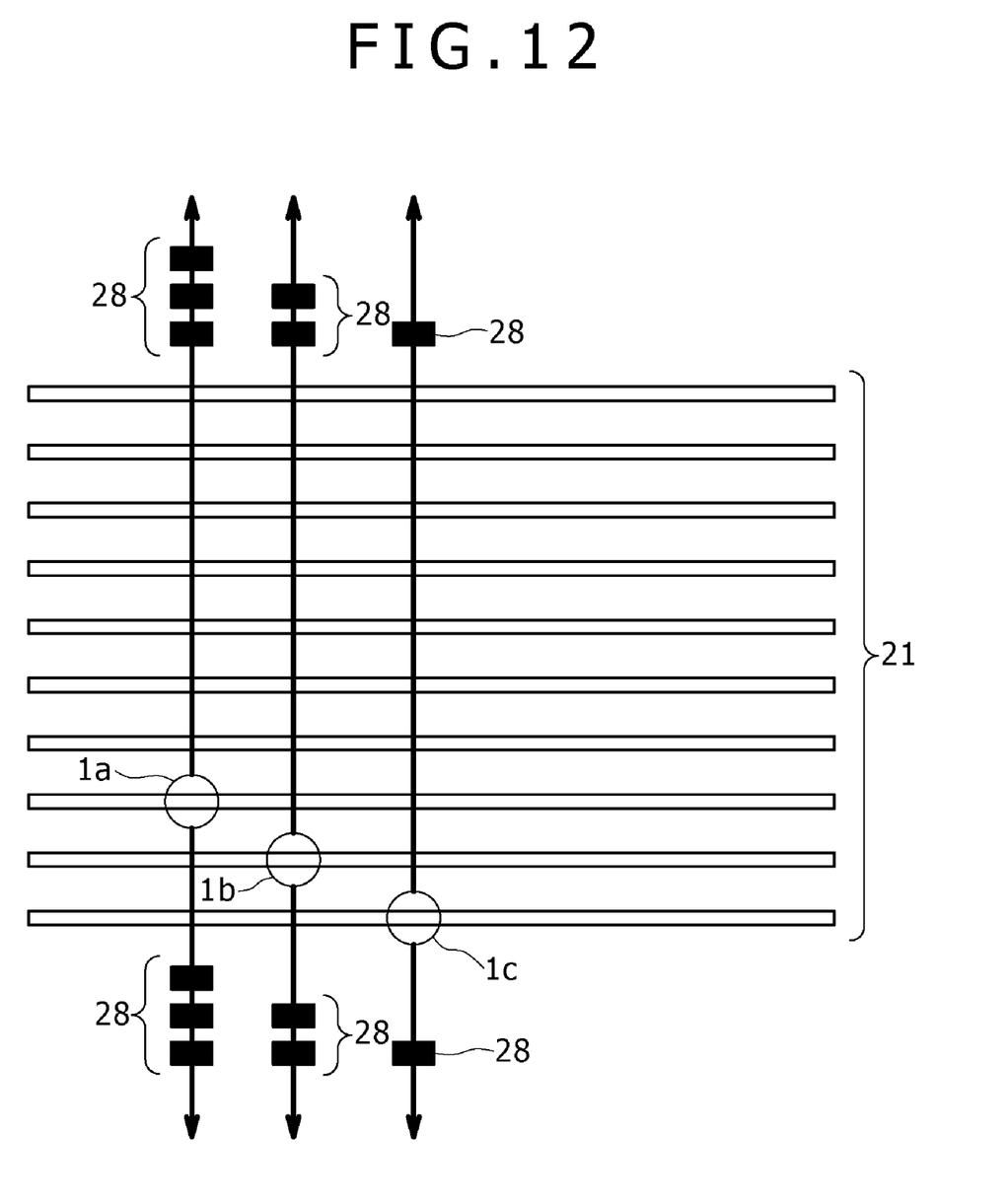
FIG. 12 is a diagram showing reference channels when a plurality of pieces of light having different wavelengths are applied.

FIG. 12 is a diagram showing reference channels when a plurality of pieces of light having different wavelengths are applied. Further, even when a plurality of pieces of light having different wavelengths are applied, by providing a plurality of reference channels 28 as shown in FIG. 12, scattering signals from the reference channels 28 and scattering signals from sample channels 21 can be easily distinguished from each other.

Incidentally, constitutions and effects other than the above in the optical measuring device according to the present embodiment are similar to those of the optical measuring device according to the foregoing first embodiment.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A measuring device comprising an optical measuring device configured to irradiate a sample flowing in a channel with light, and detect light emitted from the sample,
   wherein the light is applied while scanned at least from one side wall to another side wall of the channel in a direction of width of the channel, and scattered light at a preset threshold value or higher is detected as scattered light from edge parts in the direction of width of the channel.

2. The optical measuring device according to claim 1,
   wherein a flowing position of the sample in the channel is identified from the scattered light from the edge parts in the direction of width of the channel and scattered light from the sample.

3. The optical measuring device according to claim 1,
   wherein a plurality of channels for a sample to be measured to flow in are arranged, and further a reference channel in which the sample does not flow is disposed at an outermost part in a direction of arrangement of the channels, and
   the reference channel is also irradiated with light while the light is scanned at least from one side wall to another side wall of the reference channel in a direction of width of the reference channel, and scattered light at a preset threshold value or higher is detected as scattered light from edge parts in the direction of width of the reference channel.

4. The optical measuring device according to claim 3,
   wherein the reference channel and the other channels are different from each other in shape.

5. The optical measuring device according to claim 3,
   wherein the reference channel and the other channels are different from each other in intensity of detected scattered light.

* * * * *